(12) United States Patent
Van Houten

(10) Patent No.: US 6,215,957 B1
(45) Date of Patent: Apr. 10, 2001

(54) SYNCHRONIZER FOR FUNDUS CAMERA

(76) Inventor: Peter Arthur Van Houten, 1828 Meadowland Dr., Greenville, NC (US) 27834

( * ) Notice: Subject to any disclaimer, the term of this patent is extended or adjusted under 35 U.S.C. 154(b) by 0 days.

(21) Appl. No.: 09/456,033

(22) Filed: Dec. 3, 1999

(51) Int. Cl.[7] ....................................................... A61B 3/14
(52) U.S. Cl. ........................... 396/18; 396/180; 396/205; 351/206
(58) Field of Search .................................. 396/18, 14, 17, 396/205, 206, 180, 301, 429, 189; 348/64, 78, 370, 371; 351/206

(56) References Cited

U.S. PATENT DOCUMENTS 6,158,864 * 12/2000 Masuda et al. ...................... 351/206

* cited by examiner

Primary Examiner—W. B. Perkey
(74) Attorney, Agent, or Firm—Mills Law Firm PLLC

(57) ABSTRACT

A synchronizer is provided to establish a mechanical switching interface between an electronic digital color camera and a fundus camera for appropriately coordinating the complete opening of the color camera shutter with the energization of fundus camera flash unit, and for fully disconnecting the flash unit at the completion of an image capture sequence thereby enabling resetting of the flash unit.

5 Claims, 3 Drawing Sheets

SYNCHRONIZER FOR FUNDUS CAMERA

FIELD OF THE INVENTION

The present invention relates to cameras for the diagnosis of retinal disease, and, in particular to a system for synchronizing the flash unit of a monocular retina camera with a digital camera system.

BACKGROUND OF THE INVENTION

In the practice of opthamology and retinology, the ability to graphically view a patient's retinal area under varying conditions is extremely beneficial in the clinical diagnosis of various disorders. One type of such camera, the fundus camera, is a three-axis camera providing photographic recording of a diversity of recognized fundus presentation modes. The system also provides for black and white digital image recording, editing and archiving. Using highly corrected optical systems, brilliant imaging and high resolution is provided at the base of the retina suitable for clinical diagnosis. Most current cameras are also able to provide documentation of findings through photographic equipment, electronic image sensors and other options.

Fundus cameras are provided with a main black and white camera unit mounted at the bottom camera port. During diagnosis, the clinician may use the main camera to compile a series of images for later diagnosis and documentation, and such activity is a mainstay feature of such units. The main camera is operated from a joystick used to universally position the optics relative to the patient by depressing an actuator button at the top thereof. In such mode, the fundus camera optics and shutter system are activated for a predetermined time interval. When a signal to the fundus camera is received, the flash unit is activated to properly expose the film. If a signal is not received in such time interval, the fundus shutter system closes preventing image capture.

Oftentimes, it is desirable to supplement the black and white photographs with color photographs to enhance the diagnosis and documentation. Accordingly, the fundus camera is provided with a second camera port for the mounting and operation of a mechanical color camera. The operator can interface the color camera with the fundus camera through a connector harness for actuating the color camera from the joystick button. The system is effective in obtaining color exposures for subsequent development, printing and review. This can result is a significant time interval between examination and review of the color photographs.

With the advent of digital color cameras, there has been a pronounced interest at the clinical level to inter-face a digital color camera with the fundus camera. Such a combination would provide high quality, readily available color photographs for concurrent evaluation and diagnosis at the time of examination, as well as electronic storage for documentation and archiving. While widely accepted for many photographic purposes, the integration with the fundus camera has posed substantial problems, which heretofore have prevented effective use in the clinical practice.

Initial digital color cameras incorporated a mechanical electrical contact at the shutter that interfaced with a timing circuit of the flash unit to coordinate the flash sequence at the fully open shutter positions of both cameras. Certain difficulties were apparently created by the proprietary circuitry operating at the flash unit interface. The digital camera appears to incorporate a circuit board that requires a warmup interval before the shutter activation system on the digital camera can be operated. In ordinary usage, this is accommodated at an intermediate shutter button position wherein the circuit board is enabled, the shutter conditioned for release and the focusing system activated. In the fundus camera, the joystick button effectively bypasses the intermediate position. Accordingly, the signal to the flash unit is subject to two preconditions; the circuit warmup time and the mechanical shutter transit time. These two intervals exceed the aforementioned time interval for the fundus flash unit and the fundus shutter system closes before image capture.

The foregoing digital interface problem has been exacerbated by electronic digital cameras that have substantially replaced the mechanical versions. The latter version appears to have replaced the mechanical shutter contact with a non-publicly available electronic package. In normal operation, the mechanical shutter actuation button has two distinct, sequential positions to capture the images. In the first, partially depressed position, the main circuits are powered, the shutter is released for actuation, and the self-focusing mechanism initiated. In the second, fully depressed position, the shutter is released. The flash circuitry includes a delay to initiate the flash at the fully open shutter condition. For most applications, quality digitized images may be captured and archived.

Nonetheless, integration of the electronic digital color camera with the fundus camera has presented difficulties beyond those experienced with the mechanical version. In the fundus camera, the joystick release button is a two-position switch that bypasses the aforementioned three-position sequential button on the camera body. When interfaced, the apparent circuitry of the camera does not synchronize the flash with the shutter, generally capturing an image in the partially opened shutter condition. This appears to result from an inherent circuitry warm up time required prior to the shutter opening sequence. Manual actuation with the internal switch, fast or slow, provides sufficient staging time to allow the circuitry to operate in synchronization whereas the fundus camera sequence results in a time lag at the shutter unacceptably affecting the resultant image. Moreover, the problem of not resetting the flash unit persists. The flash units used in fundus cameras typically require fill discharge and voltage interruption to allow the power supply to reset for the next exposure. The circuitry, the details of which are not publicly available, employed in such electronic digital cameras appear to provide a sufficient residual voltage preventing the flash unit from resetting. In order to make this interface operable, the operator would have to toggle the power supply at the main switch for recycling the flash unit. Understandably, such manipulation is undesirable and laborious inasmuch as a typical examination entails a substantial number of images for capture.

Notwithstanding the foregoing problems, the desire and need at the clinician level to secure high quality digital color images on the fundus camera persists.

Accordingly, it is an object of the present invention to provide an interface between a fundus camera and a digital color camera for providing proper exposure of desired images.

Another object of the present invention is to provide an interface between a fundus camera and a digital color camera flash control that will effect resetting of the fundus camera flash unit after each exposure.

A further object is to provide synchronization between shutter opening on a digital color camera and the flash unit of a fundus camera.

A still further object is to provide a synchronizing interface between a fundus camera and an electronic digital color camera not requiring structural modification of either camera.

Yet another object is to coordinate the shutter systems of a digital color camera and a fundus camera to provide a quality focused exposure in synchronization with the flash unit on a fundus camera.

SUMMARY OF THE INVENTION

The foregoing objects are accomplished by a synchronizer in accordance with the invention wherein a mechanical switching interface is provided between an electronic digital color camera and a fundus camera for appropriately coordinating the complete opening of the color and fundus camera shutters with the energization of fundus camera flash unit, and for fully disconnecting the flash unit at the completion of an image capture sequence thereby enabling resetting of the flash unit. More particularly, the synchronizer comprises a pair of control circuits, each of which includes a mechanical relay. In a first circuit, at startup, the main circuitry and the focusing unit are continuously operated, and the shutter lock mechanism released. This configuration eliminates the system warmup time lag, provides continuous focusing, and conditions the shutter system for opening. In the second circuit, the lamp unit is conditioned for operation. Accordingly, upon depressing the fundus camera switch, the shutter release mechanism is actuated, the shutter openings for both cameras coordinated within the fundus prescribed interval corresponding to the fully open shutter positions, the flash unit is actuated, and thereafter the shutter mechanism is reset. Upon release of the fundus camera switch the circuit to the flash unit is mechanically interrupted allowing automatic resetting thereof. Tile use of the relays in both circuits nullifies the influence of the relay switching times insuring that the built in predetermined camera delay time remains matched at time of flash. The foregoing is achieved without revision of the digital camera or the fundus camera, through simple and readily available components, to achieve thereby the stated objectives.

DESCRIPTION OF THE DRAWINGS

The above and other objects and advantages of the present invention will become apparent upon reading the following detailed description taken in conjunction with the accompanying drawings in which.

DETAILED DESCRIPTION OF THE PREFERRED EMBODIMENTS

Figure 1:
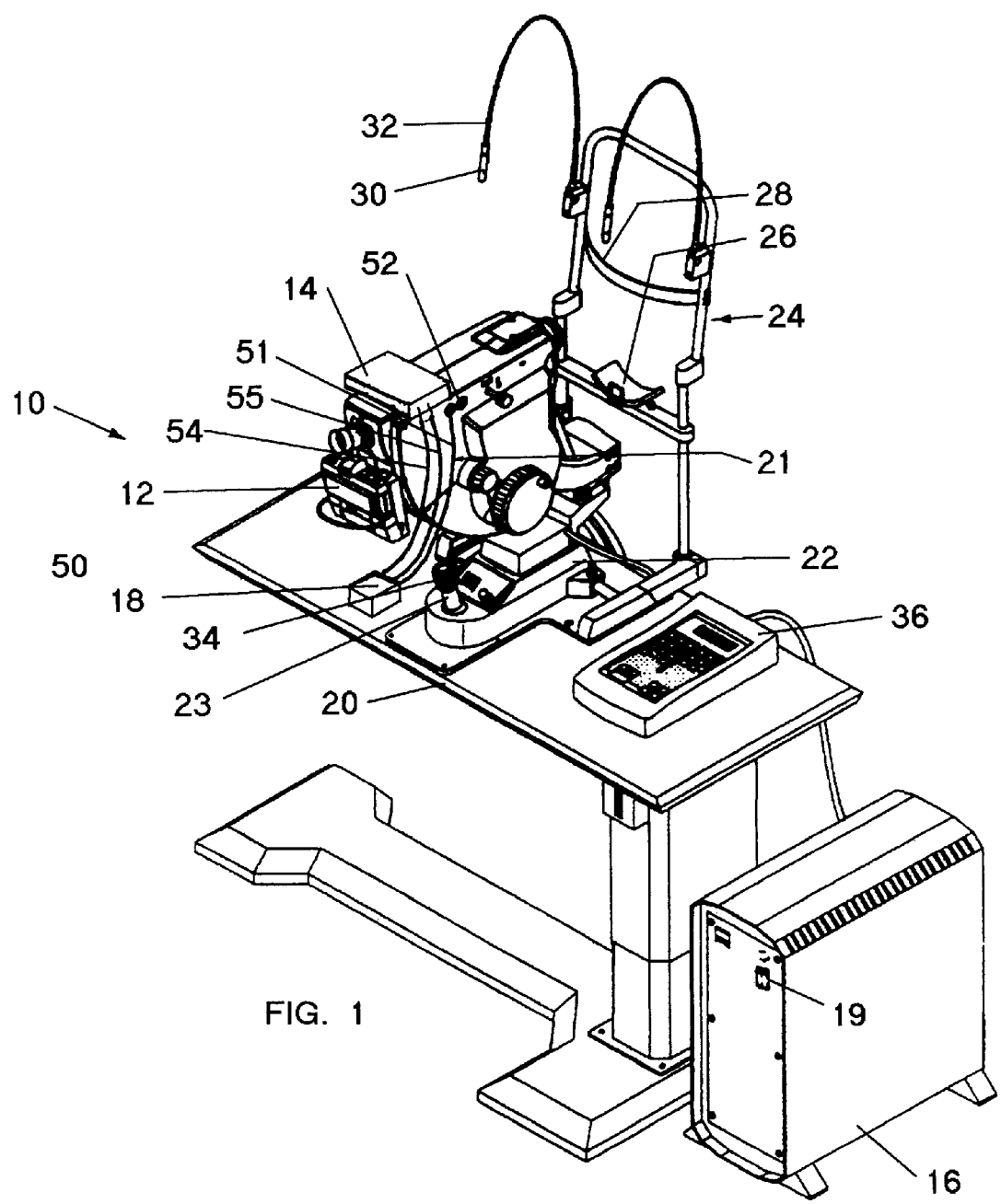
FIG. 1 is a perspective view of a fundus camera carrying a digital camera interfaced with a synchronizer in accordance with the invention.

Referring to the drawings for the purpose of describing the preferred embodiment, FIG. 1 illustrates a fundus camera (FC) 10, also known as a monocular retina camera, having a first camera 12 optically coupled thereto at a main camera port at the rear thereof, and a second camera 14, an electronic digital color camera (DCC), optically coupled thereto at an auxiliary camera port at the top thereof. The fundus camera 10 also includes a flash unit 16 coupled thereto for providing flash illumination in coordination with the cameras for capturing and recording patient information during an examination. A synchronizer 18 is interfaced between the fundus camera 10 and the digital color camera 14 by wiring harness 21.

For the purpose of the present embodiment, the fundus camera may be selected from a plurality of commercially available models. A suitable fundus camera is available from Carl Zeiss Jena GmbH of Jena Germany as model FF 450. Similarly, the digital color camera may be selected from commercially available models. A suitable digital color camera is available from Eastman Kodak Company as an adjunct to the Professional Digital Camera System, in particular a modified Nikon F3 camera body.

Both the fundus camera 10 and the digital camera 14 incorporate proprietary, non-publicly available circuitry for performing certain functions in accomplishing the objectives of the invention. The following description will accordingly proceed with reference to the synchronized interface with such functions, it being understood that those skilled in the art be able to determine the necessary specifics for integrating the selected camera.

More particularly, the fundus camera 10 is a monocular retina camera for routine clinical and diagnostic usage. The fundus camera 10 is fixedly mounted on an instrument table 20 having a motorized height adjustment, not shown. The main camera 12 may comprises a Nikon F3-HP type. The fundus camera 10 is universally coupled with an instrument base 22 including a 3D joystick 23 for universally positioning the camera optics with respect to a patient presenting for examination at a vertically adjustable head rest 24 including a vertically adjustable chin rest 26 and a forehead rest 28. Fixation lights 30 mounted on flexible necks 32 are used conventionally in the diagnosis and examination. The joystick 23 includes a camera button 34 on the top thereof for initiating a camera exposure session. A control console 36 operates in conjunction with the camera to control various functions ancillary to the present invention.

The fundus camera is also provided various mechanical controls for focusing, tilting and otherwise allowing the clinician to observe readily and accurately the desired retinal areas of the patient.

The digital camera 14 is mounted on the top optical port of the camera and may be selected for operation by controls, not shown. The synchronizer 18 comprises a housing 50 mounted on the table 20 or other suitable location having an connector cable 51 coupled with the camera port 52 on the fundus camera and cables 54, 56 connected to the main camera port and the flash port. The camera 14 is operatively connected to a digital storage unit by a supplied connector cable, not shown. The internal circuitry for the fundus camera is powered by a power supply resident in the flash unit 16. Subject to the incorporation of the synchronizer of the present invention, the fundus camera is operable for clinical and diagnostic purposes in a manner well known by those in the art.

An illustrative digital color camera for the purposes of the present invention is an unmodified Nikon F3 camera fitted with a Kodak camera back and camera winder connected to a free standing digital storage unit by an interconnect cable. As can best be ascertained for describing the preferred embodiment, the digital camera includes a control system including a main circuit board, a focusing system, a shutter system, and a flash system. Images are normally captured by a manual two-position button. In the first partially depressed position, the control system is enabled thereby enabling the circuit board, the focusing system, and the shutter system to a shutter activation position. Sequentially thereafter, in the second fully depressed position, the shutter system releases the shutter blades and, at the fully open position, sends a signal to the associated flash system. In the fundus camera flash system, the shutter system is enabled and the optics and shutter opened for a preset interval awaiting an actuation flash signal. This interval is consistent with the mechanical transit time of the digital camera shutter.

In normal usage, the shutter button is depressed in stages by the operator in a well known manner. Sufficient time is thus presented for the main circuit to warmup and for the control system to condition fully and the focusing system to align accurately with the photographic subject. Subsequent full depression of the button will thus establish the proper time interval between full shutter opening and flash unit energization. Normally, even if the operator depresses the button in a single motion sufficient staging time is effected for appropriately coordinating shutter and flash functions. However, the one stage actuation of the fundus camera button does not provide sufficient warm up time, resulting in a flash signal exceeding the fundus camera shutter opening interval thereby precluding image capture.

Figure 5:
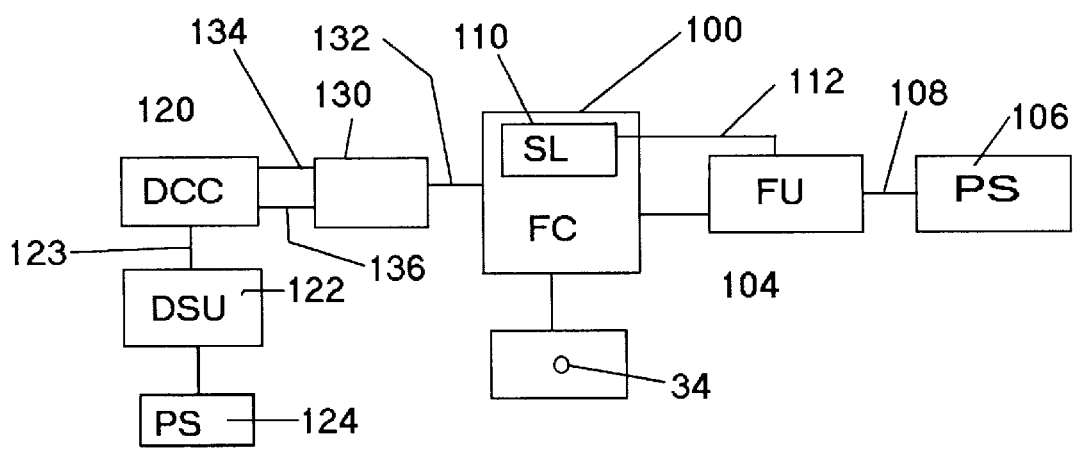
FIG. 5 is a block diagram of the synchronizer operation.

Referring to FIG. 5, there is illustrated a block diagram for the present invention for overcoming the aforementioned limitations in the interface between the digital camera and the fundus camera. Therein, the fundus camera 100 is operatively connected to the flash unit 102 by connector cable 104. The flash unit 102 is connected to external power supply 106 by cable 108 and to the flash strobe light 110 resident inside the fundus camera 100 by cable 112. The fundus camera imaging is effected by the joystick switch or button 34.

The digital camera 120 is connected to digital storage unit 122 by cable 123 and to a internal power supply 124 therein. The synchronizer 130 is coupled to the fundus camera by inlet cable 132, to the flash system of the digital camera 120 by outlet cable 134 and to the camera control system by outlet cable 136.

Figure 2:
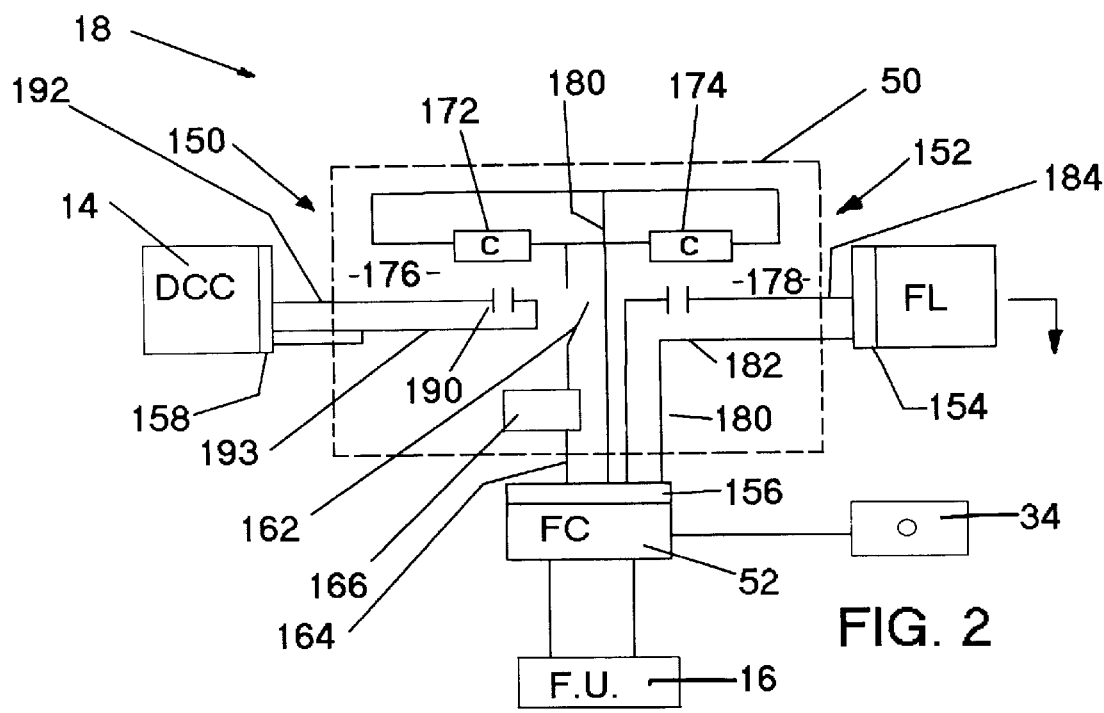
FIG. 2 is a schematic diagram of the synchronizer interfaced with the fundus camera and the digital camera.

More particularly and as shown in the schematic diagram of FIG. 2, the synchronizer 18 comprises a pair of switching circuits 150, 152 for overriding existing internal controls, and operating and coordinating the shutter opening and flash sequencing between the fundus camera and the digital camera. The first switching circuit 152 is coupled to flash connector 154 mounted on the digital camera and to the auxiliary connector 156 for the auxiliary camera port 52 on the fundus camera. The second switching circuit 150 is coupled to the main camera connector 158 on the digital camera and the connector 156 on the auxiliary camera port on the fundus camera.

The synchronizer 18 comprises a main switch 162 connected by lead 164 to a direct current power supply 166 and the auxiliary port connector 156 on the fundus camera. The power supply 166 is connected in parallel to the coils 172, 174 of normally open relays 176, 178 respectively. The coils 172, 174 are connected to ground at the fundus camera by lead 180 at the port connector 156. The normally open contacts 182 of the relay 178 are connected by lead 184 to the flash system port connector 154 on the digital camera. As discussed below, closure of the joystick button 34 on the fundus camera will activate the relay 178 closing contacts 182 completing the circuit to the digital camera flash system via lead 188 between the connector 154 and port connector 156. Leads 184 and 188, and port connector 156 comprise the outlet cable 56.

Figure 3:
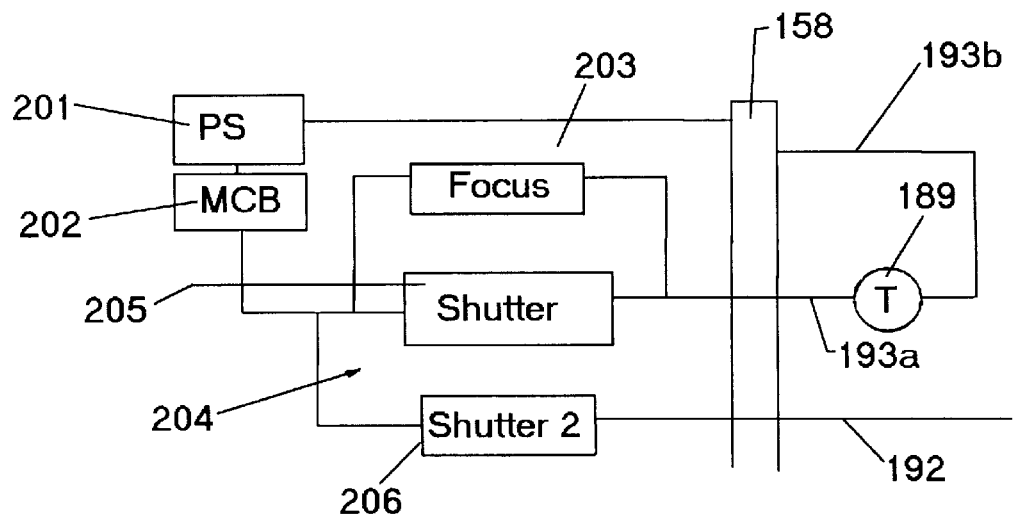
FIG. 3 is a schematic diagram of the digital camera control system.

The contacts 190 of relay 176 are connected by leads 192, 193 to the shutter port connector 158 on the digital camera. Lead 193 includes branch leads 193a and 193b at the connector 194. The leads 192, 193 and connector 158 comprise outlet cable 54 (FIG. 3). The leads 180, 184, 164 and 188 and the connector 158 comprise the outlet cable 51 from the synchronizer housing 50. Timing means 189 may be incorporated, as in line 193, to deactivate the above functions after a predetermined time.

Referring to FIG. 3, leads 193a and 193b are connected to the storage unit power supply 201, the main circuit board 202, the focus system 203 and shutter system 204. Consequently, as described below, the circuit board, the focusing system and first stage are continuously powered. Lead 192 is connected with the shutter system 204 such that contact closure activates the mechanical release of the shutter and sends an enabling signal 206 to the digital camera flash system at the fully open position, to the plug connector 154 and lines 188, 184 in switching circuit 152.

The flash system of the fundus camera to the extent known appears to incorporate a shutter system for conditioning the optics and opening the shutter to receive within a preset time interval after actuation of the joystick button 34 such that the flash is in proper sequence with the fully open shutter position. Upon closure of contacts 190, the flash signal will be transmitted to the auxiliary port 52 a predetermined time thereafter. Moreover, it appears that the flash system of the digital camera includes circuitry presenting a residual voltage to the flash unit of the fundus camera through details not present known, sufficient to prevent the resetting of the fundus camera flash unit. Accordingly, the opening of the contacts 182 mechanically interrupts power to the flash unit permitting the resetting thereof.

Lead 192 of shutter connector 158 is connected to the power supply 201 of the digital storage unit. Lead 193a appears to be connected to the circuit board 202 and the system 203. Accordingly the latter systems operate continuously until timed out by timer 189 in the synchronizer 18. When the contacts 190 are closed the second shutter is released for timed coordination with the flash unit. It will be appreciated further that the dual relays in the separate circuits have the effect of balancing the switching times associated with the individual relay, thereby retaining the predetermined time intervals between shutter opening and flash provided by the camera manufacturers. Further, by locating the contacts in an independently powered circuit, the existing camera functions operate on design voltage.

For the Nikon camera of the preferred embodiment, lead 193b is connected to pin 10, lead 193a to pin 4 and lead 192 to pin 7.

Figure 4:
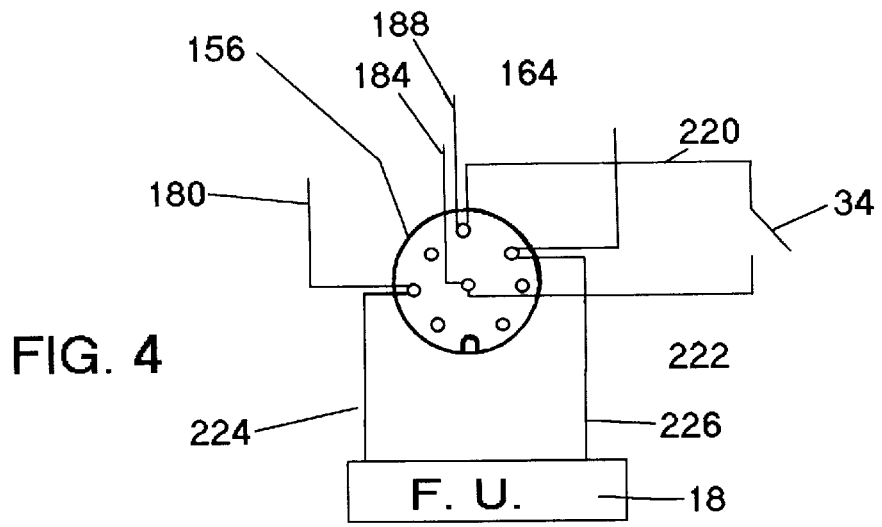
FIG. 4 is a schematic diagram of the fundus camera flash control system.

Referring to FIG. 4, the fundus camera connector 156 interfaces with the auxiliary port 52 and is connected with the joystick button 34 through internal leads 220 and 222. The internal leads 224 and 226 are connected with the flash unit 16. For the Zeiss FF449 fundus camera, leads 180, 224 are connected to pin 2, leads 164, 226 to pin 5, leads 222, 184 to pin 8 and leads 220, 188 to pin 4.

Referring to FIGS. 2 and 5, in operation, with the main power switches to the flash unit 16 and the digital storage unit closed, and the synchronizer connected, the circuit board and focusing system are powered. When the clinician desires to capture a digital color image, the appropriate mode is selected on the fundus camera controls. Thereafter, the desired image area is selected and the joystick button 34 is depressed. Thereupon the relays 178, 176 are energized closing the contacts 182, 190. After contact closure, the shutter mechanism is actuated to initiate opening of the shutter blades. At the fully open position, the flash system circuit is completed to fire the flash unit in the fundus camera in proper sequence with full shutter opening of both cameras thereby capturing a synchronized image for filing in the storage system. After shutter opening the winding mechanism is activated to rewind the film and mechanically reset the shutter mechanism. Upon release of the joystick button 34, the relays 176 and 178 are deenergized opening contacts 190 and 182. This results in a total cessation of power to the flash unit allowing the unit to reset for the next exposure.

The above embodiment has been described above with reference to a stand-alone synchronizer not requiring modifications to either camera. However, it will be appreciated that all or a portion of the functions may be integrated into either camera.

Having thus described a presently preferred embodiment of the present invention, it will now be appreciated that the objects of the invention have been fully achieved, and it will be understood by those skilled in the art that many changes in construction and widely differing embodiments and applications of the invention will suggest themselves without departing from the sprit and scope of the present invention. The disclosures and description herein are intended to be illustrative and are not in any sense limiting of the invention, which is defined solely in accordance with the following claims.

What is claimed:

1. A flash and photograph synchronizer for a fundus camera having an actuator, a resettable flash unit accommodating a flash sequence in a flash interval after actuation of the actuator and requiring power interruption thereto for resetting, and a digital camera system including an auxiliary power supply and a shutter system having a mechanical shutter movable to a fully open position in a mechanical transit time consistent with said flash interval for capturing a image at said digital camera system, said synchronizer comprising:

power supply means;

first circuit means including first mechanical switching means for operatively connecting said auxiliary power supply with said shutter system upon operation of the actuator moving said mechanical shutter to said fully open position; and second circuit means including second mechanical switching means connected between said power supply means and said flash unit for actuating said flash unit upon operation of said actuator to initiate the flash sequence during said flash interval, said second mechanical switching means effecting power interruption to said flash unit subsequent to said operation of the actuator thereby permitting the resetting thereof.

2. A synchronizer for a fundus camera for coordinating an auxiliary digital camera to record a image in timed sequence with a fundus camera actuator and a flash unit coupled to the fundus camera, the digital camera including a power supply connected to a circuit board coupled with a shutter system; comprising: first means for normally enabling said circuit board; and second means responsive to operation of the fundus camera actuator for conditioning said shutter system at a fully open position and energizing said flash unit, subsequent to said operation of the fundus camera actuator interrupting power to said flash unit.

3. A method for synchronizing image capture between a digital camera and a flash unit operatively coupled to a fundus camera wherein said digital camera includes a circuit board coupled to a power supply and a shutter system, said shutter system movable from a shutter activation position to a fully open position for capturing said image, and said flash unit includes means for energizing said flash unit and preventing subsequent energizing thereof in the absence of cessation of power thereto, comprising the steps of:

a. normally connecting said circuit board to said power supply;

b. activating said shutter system to said fully open position; and c. subsequent to said activating, effecting cessation of power to said to said flash unit and returning said shutter system to said shutter activation position.

4. In a fundus camera for recording an image from a camera port upon operation of an actuator switch having a first position and a second position, a camera system comprising: a flash unit including a main power supply operatively coupled to said fundus camera, said flash unit including control means for providing illumination in response to a signal received within a predetermined time interval and precluding subsequent illumination until cessation of power to said control means; an electronic digital camera operative coupled to said camera port, said digital camera including an auxiliary power supply coupled to a circuit board and to a shutter system, said shutter system movable responsive to operation of said actuator switch from a first position to a fully open position in a mechanical transit time less than said predetermined time interval, said digital camera providing an output signal after said mechanical transit time; a synchronizer including a switchable power supply and first circuit means and second circuit means, said first circuit means connected to said power supply, said circuit board and said shutter means for normally powering said circuit board said first circuit means including a switching device having a first switching time, said second circuit means including a second switching device having a second switching time substantially the same as first switching time, said second switching device effective for providing a cessation of power in said second circuit means in said first position of said actuator.

5. A synchronizer for coordinating a fundus camera flash unit with a digital color camera wherein said flash unit requires an enabling flash signal within a predetermined time interval after actuation and said color camera includes circuitry requiring a warmup time after actuation and a shutter transit time less than said predetermined time interval after said warmup time to transmit the flash signal, the warmup time and the shutter transit time exceeding said predetermined time interval, said synchronizer comprising: switchable power supply means normally operatively connected to said flash unit and said circuitry of said digital color camera thereby normally powering said circuitry and eliminating said warmup time such that said flash signal is received at said flash unit within said predetermined time interval.

* * * * *